United States Patent
Ando et al.

(10) Patent No.: US 6,960,363 B2
(45) Date of Patent: Nov. 1, 2005

(54) TREATMENT METHOD FOR PRESERVATION OF PLANT LEAVES

(75) Inventors: Toshio Ando, Matsudo (JP); Yoshihiro Ueda, Kamagaya (JP); Tadashi Sekiyama, Kamakura (JP)

(73) Assignee: Nikken Rentacom Company, Limited, Tokyo (JP)

( * ) Notice: Subject to any disclaimer, the term of this patent is extended or adjusted under 35 U.S.C. 154(b) by 0 days.

(21) Appl. No.: 10/053,566

(22) Filed: Jan. 24, 2002

(65) Prior Publication Data

US 2003/0017255 A1 Jan. 23, 2003

(30) Foreign Application Priority Data

Jul. 17, 2001 (JP) .................................. 2001-217150

(51) Int. Cl.$^7$ ............... B05D 5/04; B05D 1/36
(52) U.S. Cl. ............... 427/4; 427/307; 427/308; 427/314; 427/316; 427/322; 427/324; 427/352; 427/407.1; 427/439

(58) Field of Search ............... 427/4, 307, 308, 427/314, 316, 322, 324, 352, 407.1, 439

(56) References Cited

U.S. PATENT DOCUMENTS

| | | | | |
|---|---|---|---|---|
| 2,567,929 A | * | 9/1951 | Fessenden ............... | 427/4 |
| 5,677,019 A | * | 10/1997 | Carstairs et al. ............ | 428/22 |
| 5,807,604 A | * | 9/1998 | Dokkestul et al. ............ | 427/4 |
| 6,099,897 A | * | 8/2000 | Sayo et al. ............... | 427/180 |

* cited by examiner

*Primary Examiner*—Jennifer Michener
(74) *Attorney, Agent, or Firm*—Townsend and Banta

(57) ABSTRACT

A treatment method for preservation of plant leaves wherein the plant leaves are immersed in a dehydrating solvent consisting of acetone and ethyl alcohol to replace the tissue water and remove chlorophyll in the leaves by the dehydrating solvent. Thereafter, the leaves are immersed in a permeating solution containing polyethylene glycol and acetone for allowing polyethylene glycol to permeate the leaves for replacing the dehydrating solvent. Thereafter, the leaves are dyed with a coloring matter.

10 Claims, 1 Drawing Sheet

F I G. 1
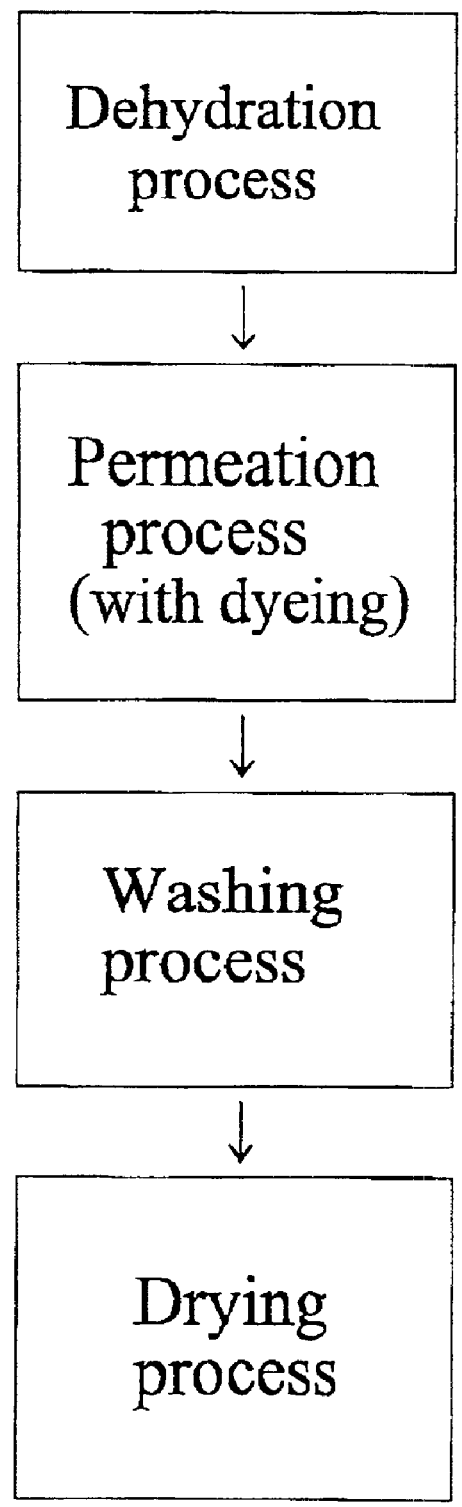

TREATMENT METHOD FOR PRESERVATION OF PLANT LEAVES

FIELD OF THE INVENTION

The present invention relates to a treatment method for preservation of plant leaves.

BACKGROUND OF THE INVENTION

A treatment method for allowing cut flowers of roses and the like to be kept appearing like natural flowers for a long period of time for the purpose of decoration is proposed, for example, in JP4-505766T2.

In this treatment method, the water in the cell tissue of cut flowers, i.e., tissue water is removed together with the coloring matter, and polyethylene glycol is allowed to permeate into the tissue once filled with tissue water, then a coloring matter being added for dyeing. The method treats the cut flowers generally through a dehydration step, permeation step and drying step.

In the dehydration step, cut flowers are immobilized in a container that has a molecular sieve spread all over its bottom and is filled with a dehydrating solvent lower in specific gravity than water, for example, an anhydrous organic solvent such as acetone.

In this step, the water in the tissue of cut flowers, i.e., tissue water is gradually dissolved into a dehydrating solvent, and simultaneously, the dehydrating solvent migrates into the tissue. So, in the cut flowers, while the tissue of cut flowers maintains its mechanical structure, the dehydrating solvent gradually replaces the tissue water, to remove it.

In the permeation step, the cut flowers are immobilized in a container filled with a permeating solution prepared by dissolving polyethylene glycol destined to permeate into the leaves, into a mixture consisting of acetone and a cellosolve. In this case, the polyethylene glycol is a mixture of polyethylene glycols adequately different in molecular weight.

In this case, in the conventional practice, a dye such as a woven fabric dye for acrylic fibers is mixed in the permeating solution, for allowing the coloring matter to permeate into the tissue of cut flowers together with polyethylene glycol, for dyeing.

After a predetermined time has elapsed in the permeation step, the permeating solution is discharged, and the cut flowers are dried in the subsequent drying step, to complete the preservation treatment of cut flowers. The cut flowers treated like this are packed in a basket or the like together with leaves for offering as merchandise.

The leaves packed with cut flowers are generally thicker than petals, and their nerves act as barriers. So, depending on leaf properties (thickness, hardness, color and the like of leaves), it can happen that dehydration cannot be achieved perfectly, and chlorophyll cannot be dissolved out sufficiently to pose a problem that the color cannot be perfectly removed.

SUMMARY OF THE INVENTION

The inventors studied intensively on the properties of other candidate solvents to be used with acetone used as a conventional dehydrating solvent, and as a result found a solvent excellent in the permeation in the dehydration step, the capability of dissolving out chlorophyll and the compatibility with the permeating solution. The object of this invention is to provide a treatment method for preservation of plant leaves for solving the aforesaid problems.

This invention for solving the aforesaid problems provides a treatment method for preservation of plant leaves, in which plant leaves are immersed in a dehydrating solvent, to replace the tissue water of the leaves by the dehydrating solvent, subsequently immersed in a permeating solution containing polyethylene glycol and acetone, for allowing polyethylene glycol to permeate for replacing the dehydrating solvent, and dyed with a coloring matter, characterized in that said dehydrating solvent is a mixture consisting of acetone and ethyl alcohol.

Acetone that can dissolve many compounds can also dissolve water well and is high in chlorophyll dissolvability, being well miscible with polyethylene glycol destined to replace the tissue water and also with the coloring mat used for dyeing. So, it is suitable as a dehydrating solvent and as a solvent used in a permeating solution. However, when acetone is used alone for leaves, it may be insufficient in permeability as a dehydrating solvent, depending on the properties of the leaves since leaves are thicker than petals and have veins functioning as barriers.

In this invention, attention is paid to ethyl alcohol that is equivalent to acetone in dehydration capability and is higher in permeability than acetone, and a mixture consisting of ethyl alcohol and acetone is used as the hydrating solvent for efficiently dehydrating the leaves.

As described above, the chlorophyll dissolvability of acetone is higher than that of ethyl alcohol and in the permeation process subsequent to the dehydration process, a permeating solution containing acetone is used. For these reasons, it is not preferable that the ethyl alcohol content of the mixture consisting of ethyl alcohol and acetone is too large. An adequate range of ethyl alcohol content is from about 20 to 50 wt %.

However, the ethyl alcohol content of the mixture consisting of ethyl alcohol and acetone can be set as required in reference to the properties of the leaves.

This invention proposes the use of a mixture obtained by adding a yellow coloring matter to a green coloring matter or blue coloring matter, as the coloring matter used for dyeing the leaves.

In this case, coloring matters for food such as Alizarine Cyanine F as the green coloring matter, Acid Blue 80(Aldrich) as the blue coloring matter and Tartrazine as the yellow coloring matter can be used.

If a mixture obtained by adding a yellow pigment such as Tartrazine to a green coloring matter such as Alizarine Cyanine F or a blue coloring matter such as Acid Blue 80(Aldrich) is added to the leaves remaining after dissolving out chlorophyll, a green color like that of natural leaves can be reproduced.

In this case, for example, a mixed food dye obtained by using Alizarine Cyanine Green F as the green dye, Acid Blue 80 (Aldrich) as the blue dye and Tartrazine as the yellow dye can be used.

If a food dye is used as described above, even if an infant, child or the like should lick the leaves or put them in the mouth, the hazard can be minimized.

BRIEF DESCRIPTION OF THE DRAWING

FIG. 1 is a flowchart showing the flow of steps in the treatment method for preservation of plant leaves in this invention.

DETAILED DESCRIPTION OF A PREFERRED EMBODIMENT

Modes for carrying out the present invention are described below.

FIG. 1 is a flowchart showing the flow of steps in the treatment method for preservation of plant leaves in this invention. The treatment method has a dehydration step, permeation step, washing step and drying step, and a coloring matter is added for dyeing in the permeation step.

At first, in the dehydration step, a molecular sieve (zeolite) for adsorbing the water dissolved from leaves was spread at a thickness of about 2 cm all over the bottom of a dehydrating container with an adequate size suitable for a batch of leaves to be treated, and leaves were immobilized in the dehydrating container. The container was filled with a dehydrating solvent consisting of equal amounts of acetone and ethyl alcohol, for treatment.

The dehydration step was carried out at room temperature (20 to 30° C.) for treatment at least for 24 hours. Even if the dehydration step was carried out for more than 48 hours, no especially beneficial point was found.

During the dehydration step, the specific gravity of the dehydrating solvent was constantly monitored using a hydrometer.

In an experiment, while the dehydration step was carried out, the specific gravity of the dehydrating solvent slowly increased, but after a certain value was exceeded, it rose sharply. Thereafter, the effect of dehydration could be little observed.

Therefore, if the specific gravity at which the effect of dehydration cannot be observed any more, i.e., the specific gravity at which the specific gravity begins to rise sharply is identified beforehand by an experiment for each mixing ratio of acetone and ethyl alcohol used together as the dehydrating solvent, the identified specific gravity can be used as a reference point for estimating that the quantity of all the water dissolved out has exceeded the water adsorability of the molecular sieve if the specific gravity of the dehydrating solvent is monitored using a hydrometer. At this time, the molecular sieve can be exchanged for a new one, to recover the dehydrating capability of the dehydrating solvent, hence to allow the continuous use of the dehydrating solvent. Therefore, the dehydration step can be carried out without waste of time. The used molecular sieve removed from the dehydrating container can be dried and reused.

In the above dehydration step, the water in the cell tissue of leaves, i.e., tissue water is gradually dissolved into a dehydrating solvent consisting of acetone and ethyl alcohol, while acetone and ethyl alcohol migrate into the tissue. So, while the tissue of leaves maintains its mechanical structure, the dehydrating solvent consisting of acetone and ethyl alcohol replaces tissue water, to achieve dehydration.

Then in the permeation step, a permeating container having leaves immobilized was filled with a permeating solution prepared by dissolving polyethylene glycol destined to permeate into the leaves, into acetone and a cellosolve, and adding a coloring matter used for dyeing, to the solution.

The permeating solution was prepared by a method of mixing polyethylene glycols different in molecular weight (for example, PEG1000 and PEG400), for example, at the following ratio, and dissolving the mixture into a solvent such as a mixture consisting of acetone and a cellosolve (1:1).

Example of Permeating Solution
  PEG1000 500 g
  PEG 400 100 ml
  Solvent consisting of acetone and a cellosolve (1:1) to make one liter in total.

The permeating solution prepared at the above ratio becomes a solid at lower than 15° C. So, if it is heated in a water bath or incubated for treatment at a temperature higher than the solidifying temperature, for example, about 25 to 35° C. for 24 hours, the best permeation effect can be achieved.

Theoretically, permeation treatment at a higher temperature can shorten the treatment time, but according to an experiment, polyethylene glycol permeated more uniformly with treatment at room temperature (20 to 30° C.) for 24 hours than treatment at 50° C. for 12 hours.

Examples of the Coloring Matter used for Dyeing in the Permeation Step

To reproduce the natural green color as observed in plant leaves, the following coloring matters were used.

When Alizarine Cyanine Green F only was used as a green coloring matter, an unnatural blue tone occurred. So, when Tartrazine as a yellow coloring matter was added to Alizarine Cyanine Green F used as a basic color, a natural green color as observed in the leaves of plants could be reproduced.

Also when Tartrazine as a yellow coloring matter was added to Acid Blue 80 (Aldrich) used as a basic color instead of the above Alizarine Cyanine Green F used as a basic color, a natural green color as observed in the leaves of plants could be reproduced.

In this embodiment, the mixed coloring matter is added to the permeating solution only for dyeing in the permeation step only. However, it can also be added to the dehydrating solvent as well as to the permeating solution, for dyeing in both the dehydration step and the permeation step.

Next in the washing step, the leaves delivered from the permeation step were immersed in the same solvent consisting of acetone and a cellosolve (1:1) as the solvent of the permeation step, for a predetermined time, for example, 2 to 8 hours, for washing.

In his case, if the leaves are immersed in the solvent for a time longer than necessary, the polyethylene glycol permeating into the cell tissue of the leaves in the permeation step also flows out. Therefore, time control is necessary. For the time control, the immersion time can be decided in reference to such conditions as the kind and sizes of leaves and experimentally preliminarily obtained data.

Subsequently to the washing step, the leaves are dried in any adequate drying step as described in the aforesaid prior art, to obtain leaves that can be kept appearing like natural leaves for a long period of time for the purpose of decoration. They can be packed together with cut flowers into a basket or the like, for offering as merchandise.

INDUSTRIAL APPLICABILITY

The present invention as described above has the following advantages.

a. Attention is paid to ethyl alcohol that is equivalent to acetone in dehydrating capability and is higher than acetone in permeability, and a mixture consisting of ethyl alcohol and acetone is used as a dehydrating solvent for better dehydration of leaves. In addition, the capability of acetone to dissolve chlorophyll is used for better removal of chlorophyll as well as water.

b. If a mixture obtained by adding a yellow pigment such as Tartrazine to a green coloring matter such as Alizarine Cyanine F or a blue coloring matter such as Acid Blue 80(Aldrich) is added to the leaves remaining after dissolving out chlorophyll, a green color like that of natural leaves can be reproduced.

c. As a result, leaves free from irregular dyeing, having a natural hue and capable of being preserved for a long time can be obtained.

d. In the case where a food dye is used as the coloring matter as described above, even if an infant, child or the like should lick the leaves or put them in the mouth, the hazard can be minimized.

What is claimed is:

1. A treatment method for preservation of plant leaves, in which plant leaves are immersed in a dehydrating solvent, to dissolve out chlorophyll and replace the tissue water of the leaves by the dehydrating solvent, subsequently immersed in a permeating solution containing polyethylene glycol and acetone, for allowing polyethylene glycol to permeate for replacing the dehydrating solvent, and dyed with a coloring matter, wherein the dehydrating solvent is a mixture consisting of acetone and ethyl alcohol.

2. A treatment method for preservation of plant leaves, according to claim 1, wherein the coloring matter is obtained by adding a yellow coloring matter to a green coloring matter or blue coloring matter.

3. A treatment method for preservation of plant leaves, according to claim 1, wherein the coloring matter is a food dye.

4. A treatment method for preservation of plant leaves, according to claim 2, wherein the green coloring matter is Alizarine Cyanine Green F.

5. A treatment method for preservation of plant leaves, according to claim 2, wherein the blue coloring matter is Acid blue 80.

6. A treatment method for preservation of plant leaves, according to claim 2, wherein the yellow coloring matter is Tartrazine.

7. A treatment method for preservation of plant leaves, according to claim 2, wherein the coloring matter is a food dye.

8. A treatment method for preservation of plant leaves, according to claim 3 wherein the green coloring matter is Alizarine Cyanine Green F.

9. A treatment method for preservation of plant leaves, according to claim 3, wherein the blue coloring matter is Acid blue 80.

10. A treatment method for preservation of plant leaves, according to claim 3, wherein the yellow coloring matter is Tartrazine.

* * * * *